United States Patent [19]

Valentino

[11] 4,235,350
[45] Nov. 25, 1980

[54] BED SIDE RAIL CONTAINER WITH REMOVABLE LINER

[76] Inventor: Pearl T. Valentino, 846 50th St., D-2, Brooklyn, N.Y. 11220

[21] Appl. No.: 67,673

[22] Filed: Aug. 20, 1979

[51] Int. Cl.³ .............................................. B65D 90/04
[52] U.S. Cl. .................................. 220/404; 206/806; 248/95; 224/42.46 R
[58] Field of Search ................. 220/404, 403, 401, 18; 206/806; 248/95; 224/42.46 R

[56] References Cited

U.S. PATENT DOCUMENTS

| 3,608,712 | 9/1971 | Savoie | 220/404 X |
| 4,154,383 | 5/1979 | Honatzis | 206/806 X |

Primary Examiner—George T. Hall
Attorney, Agent, or Firm—Richard L. Miller

[57] ABSTRACT

A waste container for hanging on a bed side rail of a hospital patient; including a rigid plastic box that is open on top and a disposable paper bag fitted therein, a pair of straps snap-fastened to the box for being suspended around the bed side rail.

2 Claims, 3 Drawing Figures

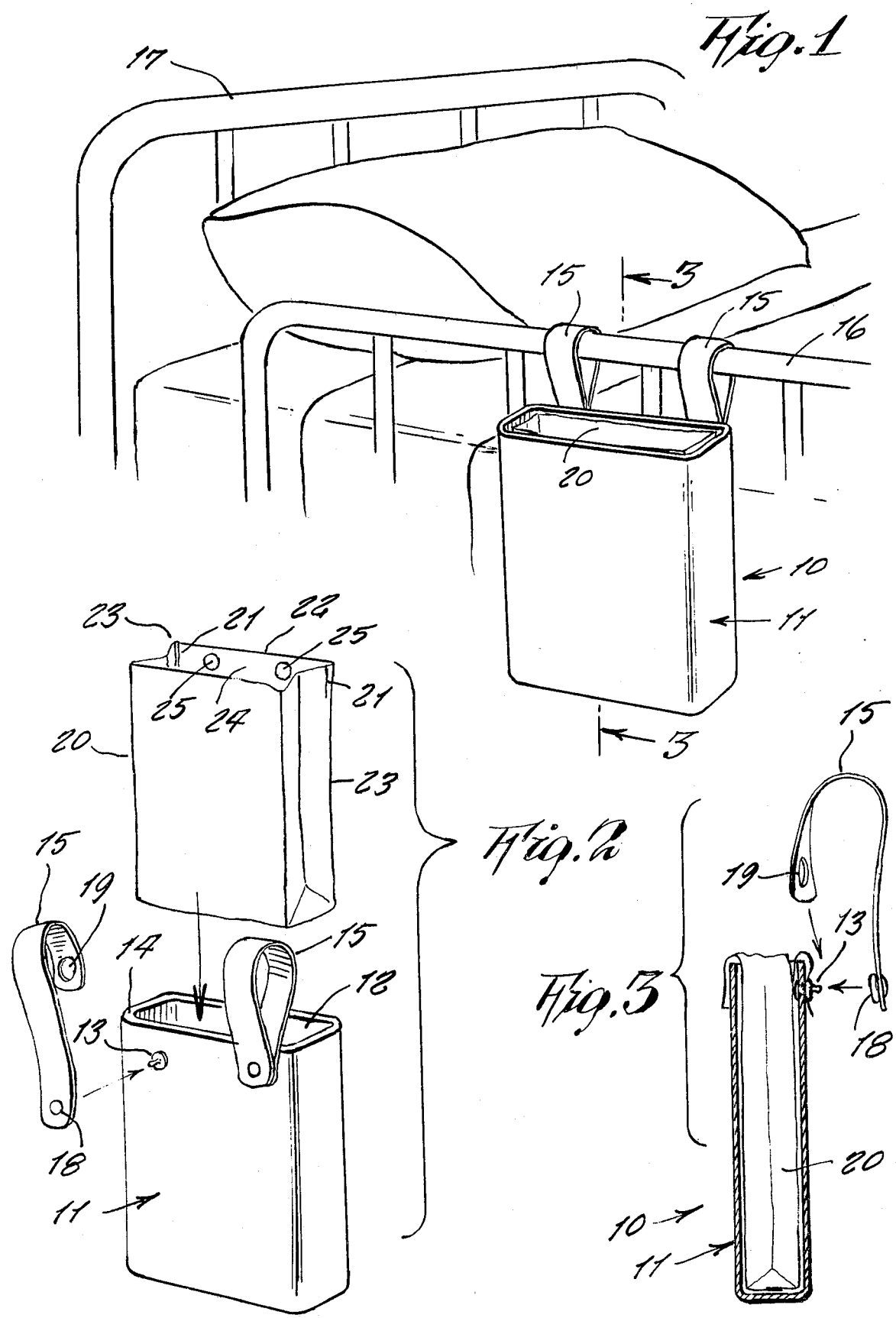

_4,235,350_

BED SIDE RAIL CONTAINER WITH REMOVABLE LINER

BACKGROUND OF THE INVENTION

This invention relates generally to hospital room accessories. More specifically it relates to waste baskets.

It is well known to those persons who attend to patients' needs in a hospital, that the rooms and wards of such institutions are equipped with waste baskets in a conventional manner for deposit therein of litter such as used paper napkins, paper cups and the like. But such waste baskets, even if placed near a bed, are often missed by litter thrown from the patient in bed, so that the attendent is obliged to pick it up and clean up afterwards. This situation is accordingly in want of an improvement.

SUMMARY OF THE INVENTION

Therefore it is a principal object of the present invention to provide a litter basket or container which is placed close enough to a bed-ridden patient so that he can reach the same with his hand and directly therefrom place litter in the basket instead of tossing at it from some distance away, and possibly missing his aim.

Another object is to provide a basket or container which accordingly is attached to a side rail of a bed so as to be within arms reach, and which includes a disposable bag liner, so that the container remains clean while only the bag liner is changed.

Still another object is to provide a container which can be attached to a wheel chair or armchair in a home, for party gatherings.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a perspective view of the invention installed on a bed side rail.

FIG. 2 is a view of the plastic container and disposable paper bag placable therein.

FIG. 3 is a side cross sectional view on line 3—3 of FIG. 1.

DETAILED DESCRIPTION OF PREFERRED EMBODIMENT

Referring now to the drawing in greater detail, the reference numeral 10 represents a handy bed side rail container, according to the present invention, wherein there is a semi-hard plastic box 11 having an opening 12 on the top. It may be molded in clear or opaque attractive colors, having a surface that will not glare strong light, and for most practical purposes measures about twelve to fourteen inches deep, nine inches wide, and two and one half inches wide so that it does not protrude obtrusively from its installed location. All corners are gently rounded so to prevent injury thereon.

A pair of male snap fastener elements 13 are affixed on an outer side wall thereof, and located near an upper edge 14. A pair of straps 15 attachable to the elements 13, serve to support the container from a side rail 16 of a hospital bed 17.

Each strap may be made of soft plastic, attractively colored and measures about two inches wide and nine inches long. A female snap fastener element 18 is mounted near one end, and a large circular hole 19 is near the other end, so that the male snap fastener element 13 is passed therethrough before engaging the female element 18, as indicated in FIG. 3.

A liner 20, shown in FIG. 1, is of the same size as the box interior and fits therein, comprising a paper bag or plastic that can be disposed when filled with litter and is then replaced with a new bag. However as shown in FIGS. 2 and 3, the liner can be made longer than the depth of the box so that the upper end of the bag drapes over the top edge 14 and protects it from contamination by the litter.

The bag accordingly is designed with a pair of short slits 21 extending downwardly from a top edge 22 thereof, the slits being located along the vertical folds 23 that define the side edges of one of the side panels 24 of the bag, so that the upper end of the panel 24 can be folded over the box top edge 14. A pair of large holes 25 in the folded over upper portions of panel 24 align with the male snap fastener elements 13 which also pass therethrough prior to engagement with female elements 18, as also clearly shown in FIG. 3. The remaining upper end of the bag is downwardly draped over the other three sides of the box upper edge 14, as shown. The bag, thus held between the snap fastener elements, cannot be accidently pushed down into the box.

In operative use, it is now evident that the container 10 is in handily reached by a patient for deposit of used napkins, medication paper cups, used alcohol sponges, and other litter. The container does not protrude for from the bed for interferring with persons passing by. Yet it holds a large amount of litter. The small mouth opening thereof eliminates odors outward therefrom. Being located high up, it is more convenient for an attendant to clean out than a wastebasket down on a floor.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

I claim:

1. A handy bed side rail container, comprising in combination, a plastic box, a paper bag liner inside said box and a pair of straps for attachment around a side rail of a bed wherein said box has an opening on its top, said box being generally flat and having male snap fastener elements near its upper edge for attachment to female snap fastener elements on said straps.

2. The combination as set forth in claim 1 wherein said bag includes means for draping over said box upper edge and securement between said snap fastener elements.

* * * * *